United States Patent [19]

Durlach

[11] 4,199,601
[45] Apr. 22, 1980

[54] DERIVATIVES OF TAURINE HAVING REINFORCED NEURO-MUSCULAR ACTIVITY

[75] Inventor: Jean P. Durlach, Paris, France

[73] Assignee: La Cooperation Pharmaceutique Francaise, Melun, France

[21] Appl. No.: 888,202

[22] Filed: Mar. 20, 1978

[30] Foreign Application Priority Data

Mar. 23, 1977 [FR] France .................................. 77 08692

[51] Int. Cl.² ................ C07C 143/155; A61K 31/195
[52] U.S. Cl. ................................ 424/315; 260/513 N
[58] Field of Search ................... 260/513 N; 424/315

[56] References Cited

U.S. PATENT DOCUMENTS

| 3,232,968 | 2/1966 | Schenck et al. | 260/513 N |
| 3,344,174 | 9/1967 | Broussalian | 260/513 N |
| 3,544,597 | 12/1970 | Killam | 260/513 N |
| 3,960,918 | 6/1976 | Schroeck | 260/513 N |

FOREIGN PATENT DOCUMENTS 1090779 11/1967 United Kingdom ............... 260/513 N

OTHER PUBLICATIONS

Teraoka, "Hoppe–Seyler Zeitscrift fur Physiologische Chemie", 145, 242 (1925).

Primary Examiner—Joseph E. Evans
Attorney, Agent, or Firm—Lewis H. Eslinger

[57] ABSTRACT

The present invention relates to derivatives of taurine represented by the general formula:

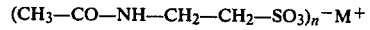

in which M is an alkali- metal such as potassium, lithium or an alkaline-earth metal such as calcium and magnesium, of valency n, n being equal to 1 or 2, or the quaternary ammonium cation of a nitrogenous organic base, to the process for preparation thereof from taurine and application thereof as drugs having a reinforced neuromuscular activity.

5 Claims, No Drawings

DERIVATIVES OF TAURINE HAVING REINFORCED NEURO-MUSCULAR ACTIVITY

The invention relates to new derivatives of taurine having a reinforced neuro-muscular activity and to use thereof as drugs.

The compounds according to the invention are represented by the general formula:

$$(CH_3-CO-NH-CH_2-CH_2-SO_3)_n^- \; M^+$$

in which M represents an alkali-metal or alkaline-earth metal, of valency n, n being equal to 1 or 2, or the quaternary ammonium cation of a nitrogeneous organic base.

The cations represented in the above formula by M+ are preferably those which give the compounds according to the invention reinforced neuro-muscular properties: i.e., for example lithium, caesium, rubidium, calcium, magnesium, among the alkali- or alkaline-earth metals, or zinc, and, among the nitrogenous organic bases, pyridoxine, ajmaline, sparteine, etc . . .

The salts of N-acetyl taurine present new properties over taurine, and in particular an increased power of cellular penetration, this in particular increasing the neuro-muscular activities of this sulfonic aminoacid. In fact, N-acetylation allows an increase in the cellular penetration of various other sulphured organic compounds: penicillamine, homocysteine or its thiolactone for example, without altering the biological activity thereof. Now, although taurine exerts major physiological effects on the nervous system which are considerable enough to class this aminoacid among the neuro-mediators or neuro-modulators, these effects can be observed in practice only by the administration "in situ" of the aminoacid.

On the other hand, N-acetylation, a conventional process of detoxification, effectively reduces the toxicity of certain of these sulphured compounds like, moreover, cysteamine.

Among the metal salts according to the invention, that of potassium is interesting as the taurine acts on the permeability of the membrane by maintaining this ion in the cell; those of lithium, caesium and rubidium exert central nervous effects enabling the neuroleptic effects of the taurine to be increased; the salts of magnesium and calcium act on the stability of the membrane.

Among the organic salts according to the invention, pyridoxine occurs at various essential stages of the metabolism of the taurine and the various organic bases which have been fixed on the acetyltaurine enable their complementary and additive pharmacodynamic properties to be added thereto.

The salts according to the invention are generally prepared by a process similar to the process for the preparation of the acetyltaurinate of sodium by: M. TERAOKA; Hoppe-Seyler Zeitschrift fur Physiologische Chemie 145 242 (1925); i.e., by action of acetic anhydride on the taurine in the presence of the base corresponding to the salt which it is desired to obtain, at the boiling temperature of the mixture.

The examples given hereinbelow illustrate the process for preparation of the compounds according to the invention.

EXAMPLE 1

Preparation of N-acetyl-taurinate of sodium $$CH_3-CO-NH-CH_2-CH_2-SO_3Na$$

In the three-necked, 4-liter flask, 1.5 liters of water then 64 g of sodium hydroxide are introduced with stirring; after dissolution, 200 g of pure taurine are then introduced all at once. 1 liter of acetic anhydride is then poured through the bromine funnel so that the temperature does not exceed 70° C. Heating is then effected for 2 hours to reflux and concentration is effected in vacuo to a maximum. The liquid residue is transvased into procelain vat and is dried in vacuo for 4 hours at 100° C. The solid obtained is ground and the fine powder is rendered pasty once in 1 liter of acetone and once in 1 liter methanol. Oven-drying is effected. Whitish-cream crystals are obtained.

| Yield: 66% Analysis: | Calculated (%) | Found (%) |
|---|---|---|
| Na | 12.17 | 12.21 |
| N | 7.40 | 7.51 |

EXAMPLE 2

Preparation of N-acetyl-taurinate of potassium $$CH_3-CO-NH-CH_2-CH_2-SO_3K$$

In a flask equipped with magnetic stirring means, are introduced 5 g of taurine, 3 g of potash in solution in 80 of water and 25 ml of acetic anhydride which are added slowly. The temperature rises to 40° C. Heating is then effected for 2 hours to reflux (90° C.). The mixture is completely concentrated in vacuo and the residue is recrystallized twice in 500 ml of 95% ethyl alcohol and rendered pasty in 200 ml of hot methanol, then dried. 7 g of a white solid is obtained.

M.P. 212° C. Yield: 60%

| Analysis: | Calculated (%) | Found (%) |
|---|---|---|
| C | 23.41 | 23.42 |
| H | 3.93 | 4.02 |
| N | 6.83 | 7.08 |
| K | 19.02 | 19.11 |

EXAMPLE 3

Preparation of N-acetyl-taurinate of lithium $$CH_3-CO-NH-CH_2-CH_2-SO_3Li$$

5 g of taurine and 3.4 g of lithia are mixed with stirring in 50 ml of water. 30 ml of acetic anhydride are then rapidly introduced, heating is effected for 1 hour to reflux, complete concentration is effected in vacuo, the residue is recrystallized in a dilute alcoholic mixture. Whitish-cream crystals are obtained.

| Yield: 70% Analysis: | Calculated (%) | Found (%) |
|---|---|---|
| Li | 4.04 | 4.31 |
| N | 8.09 | 8.21 |
| Dosage per HClO$_4$:99% | | |

EXAMPLE 4

Preparation of N-acetyl-taurinate of magnesium $(CH_3CO-NH-CH_2-CH_2SO_3)_2 \, Mg$ 10 g of pure magnesia and 150 ml of water then 15 g of taurine and, finally, 150 ml of acetic anhydride are introduced. The mixture is taken to reflux for one hour, concentrated in vacuo to a maximum, the solid is dried in vacuo at 100° C. for 24 hours and is rendered pasty in 200 ml dry and hot methanol. White crystals are obtained.

Yield: 65%

| Analysis: | Calculated (%) | Found (%) |
|---|---|---|
| Mg | 6.73 | 6.94 |
| N | 3.93 | 3.81 |
| Dosage per EDTA: 102% | | |

EXAMPLE 5

Preparation of N-acetyl-taurinate of calcium $(CH_3-CO-NH-CH_2-CH_2SO_3)_2 \, Ca$ In a three-necked 500 ml-flask are introduced 50 g of permuted water, 25 g of taurine and 10 g of calcium carbonate. Heating is effected to 100° C. and is then stopped. 60 ml of acetic anhydride are poured so as to maintain a slight reflux. At the end of pouring, heating is effected for 2 hours to 105° C., the mixture is concentrated to dryness, oven-drying is effected in vacuo for 16 hours at 120° C. The residue is rendered pasty in 50 ml of acetic acid, filtered and washed 3 times in 50 g of acetone; it is dried and 17 g of a white, 98% pure solid is obtained, the melting point of which is higher than 250° C.

The acute toxicity of the compounds according to the invention was studied by the intraperitoneal route in the male mouse. The results obtained were as follows:

The $LD_{50}$ by the intraperitoneal route in the male mouse is 3234 mg/kg for N-acetyltaurinate of potassium; 3875 mg/kg for the N-acetyltaurinate of lithium; 1604 mg/kg for the N-acetyltaurinate of calcium; 1709 mg/kg for the N-acetyltaurinate of magnesium.

The $LD_{50}$ by the oral route in the male mouse is 8170 mg/kg for the N-acetyltaurinate of potassium; 6630 mg/kg for the N-acetyltaurinate of lithium; 13230 mg/kg for the N-acetyltaurinate of calcium; 17400 mg/kg for the N-acetyltaurinate of magnesium.

The products of Examples 2, 3 and 4 have been the subject of a pharmacological study and their neuromuscular activity has been demonstrated by the following six tests, according to which the taurine proved to be without any activity:

1. The investigation behaviour of the mouse was studied by the "Holed board" test (Boissier and Simon; Arch. Int. Pharmacodyn. 1964, 147, 3–4),
2. The study of the spontaneous motility of the mouse was made by using Boissier's photoelectric actimeter.
3. The study of the motility of the mice was also made by using Boissier's photoelectric actimeter, after amphetamine-acetyltaurinate interaction according to the invention: the mice are treated simultaneously with 10 mg/kg (IP) of dextrorotatory amphetamine and with an optimal dose of acetyltaurinate.
4. A study of the hypothermia in the mouse was effected by determining the rectal temperature of the mice 30 mins. before the intraperitoneal administration of the product, at the moment of this administration, then 30 mins., 1 hour, 2, 3 and 4 hrs. after the injection of the product.
5. The study of the hypothermia after amphetamine-acetyltaurinate interaction according to the invention was made according to the same method as previously in the mouse, the animals being treated simultaneously with 30 mg/kg (IP) of dextrorotatory amphetamine and with an optimal dose of the product to be tested.
6. A test was also made of the appetite - and thirst-depressant activities in the rat.

The results of the pharmacological study are as follows:

The N-acetyl-taurinate of lithium provokes in the mouse a very clear increase in the investigation behaviour and in the motility in free condition; an increase in the motive agitation and an increase in the amphetaminic excitation. It also provokes in the mouse a significant hypothermia which is completely eliminated by the injection of amphetamine simultaneously with the product; in the rat, it provokes very clear appetite-and thirst-depressant actions (very substantial reduction in the taking of food and drink consumed).

Moreover, the toxicity of the lithium cation in the N-acetyl-taurinate of lithium is significantly reduced with respect to the corresponding toxicity in the lithium carbonate, reference body, as shown in the following Table which gives the toxicities by the oral and intraperitoneal routes, in the male mouse, of the lithium carbonate and of the N-acetyl-taurinate of lithium, in mg of lithium/kg.

| | $LD_{50}$ IN THE MALE MOUSE | |
|---|---|---|
| | Oral route | Intraperitoneal route |
| Lithium carbonate | 162 mg/kg | 88 mg/kg |
| N-acetyl-taurinate of lithium | 266 mg/kg | 155 mg/kg |

The N-acetyl-taurinate of potassium provokes an increase in the investigation behaviour in the mouse, not proportional to the dose, a slight increase in the motive agitation and a reduction in the amphetaminic excitation.

The N-acetyl-taurinate of magnesium provokes in the mouse an increase in the motive agitation at a low dose (100 mg/kg) and, on the contrary, a very clear reduction of this agitation at high dose (200 mg/kg). It also provokes a reduction in the amphetaminic excitation and a very considerable reduction in the maximum rectal temperature, 2 hours after the injection of the product, this action being completely eliminated by simultaneous injection of amphetamine, 1 hour after the injection.

The N-acetyltaurinate of calcium provokes, in the mouse, a reduction in the motive agitation at a low dose (100 mg/kg), an increase in the exploratory activity, a significant reduction in the rectal temperature; on the other hand, it does not modify either the amphetaminic excitation nor hyperthermia.

For use in human therapy, the compounds according to the invention may be presented in the following forms of administration:

by the oral route, such as tablets, sugar-coated pills, capsules, gelatin-coated capsules, solutions, containing the active product at the unitary dose of 0.30 to 1 g and, for the solutions, from 0.5 to 5 g per 10 ml, the dose to be administered daily being from 0.30 and 10 g and preferably from 1.5 to 2 g;

by the parenteral route, such as injectable solutions packaged in ampoules, containing from 0.5 to 5 g of active product per ampoule;

by the topical route, such as lotions, creams, ointments.

The compounds according to the invention are used for treating neuro-muscular affections.

The N-acetyl taurinate of potassium may be used as musculo-myocardium stimulant, particularly in arterites. The N-acetyl taurinate of magnesium is useful in all indications in magnesium-therapy, particularly as neurosedative and in epilepsy, and as tissue protector, particularly antianoxic and antiaggregant.

The N-acetyl-taurinate of calcium is useful in all indications in calcium-therapy, in particular as neurosedative and drug treating fatigue.

The N-acetyl-taurinate of lithium may be used in all indications of lithium, with less danger of toxic accidents and an increased neurotropic activity.

The following observation is given by way of example: Mr. André V., aged 32 years, has been treated for 7 years for a neuro-muscular hyperexcitability, with a wide range of neuro-vegetative disorders. He presents critical phenomena of lipothymia type, anxious crises with paroxysmal tachycardia. He has had four grand mal epileptic crises.

The electroencephalogram shows slow waves, the ionic balance is normal except for a discrete reduction (51 mg/litre) of the erythrocyte magnesium.

Earlier treatments associating phenobarbital, β-blocking agents, various types of oral magnesium therapy, have given partial results. A treatment by the N-acetyl taurinate of magnesium associating, the first ten days, a venous perfusion in isotonic serum with glucose added of 1 g at the regular daily dose of 1.5 g per os (three doses of 0.5 g) brings a complete recovery of the general state with, in particular, disappearance of the critical phenomena, verified with a recession of 13 months.

What we claim is:

1. Derivatives of taurine represented by the formula:

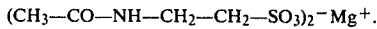

$(CH_3-CO-NH-CH_2-CH_2-SO_3)_2{}^-Mg^+$.

2. A compound according to claim 1 used as drugs, in particular as agents having a reinforced neuro-muscular activity.

3. Pharmaceutal compositions containing as active ingredient a compound according to claim 1 associated with a suitable excipient for administration by the oral, parenteral or local route.

4. Orally administered forms of the compositions according to claim 3, containing the active ingredient at the unitary dose of 0.30 g to 1 g for capsules, sugar-coated pills, tablets, gelatin-coated capsules, and from 3 to 5 g/10 ml for the solutions.

5. Parenterally administered forms of the compositions according to claim 4, containing the active ingredient at a dose of 0.5 to 2 g per injectable ampoule.